United States Patent
Bruening et al.

(10) Patent No.: US 6,576,678 B1
(45) Date of Patent: Jun. 10, 2003

(54) W/O EMULSION BASES

(75) Inventors: Stefan Bruening, Duesseldorf (DE); Achim Ansmann, Erkrath (DE); Gabriele Strauss, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/719,929

(22) PCT Filed: Jun. 15, 1999

(86) PCT No.: PCT/EP99/04123

§ 371 (c)(1),
(2), (4) Date: Feb. 9, 2001

(87) PCT Pub. No.: WO99/67016

PCT Pub. Date: Dec. 29, 1999

(30) Foreign Application Priority Data

Jun. 24, 1998 (DE) .......................... 198 28 081

(51) Int. Cl.⁷ .............. B01F 3/08; B01F 17/34; A61K 7/00; A61K 9/107
(52) U.S. Cl. .............. 516/22; 516/29; 516/31; 516/918; 424/401; 424/59; 514/939; 514/941; 514/943
(58) Field of Search .............. 516/29, 22, 31, 516/918; 514/939, 941, 943; 424/59, 401

(56) References Cited

U.S. PATENT DOCUMENTS

| | | | |
|---|---|---|---|
| 4,172,887 A | 10/1979 | Vanierberghe et al. | 424/70.17 |
| 5,705,169 A | 1/1998 | Stein et al. | 424/401 |
| 5,730,960 A | 3/1998 | Stein et al. | 424/59 |
| 5,840,943 A | 11/1998 | Ansmann et al. | 554/166 |
| 6,221,370 B1 * | 4/2001 | Wadle et al. | 514/937 |
| 6,316,030 B1 * | 11/2001 | Kropf et al. | 424/401 |
| 6,348,202 B1 * | 2/2002 | Wadle | 424/59 |

FOREIGN PATENT DOCUMENTS

| | | |
|---|---|---|
| DE | 11 65 574 | 3/1964 |
| DE | 20 24 051 | 12/1971 |
| DE | 195 09 301 | 9/1996 |
| EP | 0 693 471 | 1/1996 |
| EP | 0 694 521 | 1/1996 |
| EP | 0 818 450 | 1/1998 |
| FR | 2 252 840 | 8/1975 |
| GB | 962919 | 7/1964 |
| GB | 1 333 475 | 10/1973 |
| WO | WO 95/34528 | 12/1995 |

OTHER PUBLICATIONS

Hawley's Condensed Chemical Dictionary, 11ᵗʰ Edition, edited by Sax and Lewis, Sr. (Van Nostrand Reinhold Co, NY, NY, copyright 1987) Oct. 1989, pp. 126, 567, 682, 797, 798.*
Zeidler, Fette–Seifen–Anstrichmittel, vol. 87, (1985), Month unknown, pp. 403–408.
Wallat, et al., Parfümerie und Kosmetik, vol. 75, (1994), Month unknown, pp. 768–771.
Lochhead, et al., Encyclopedia of Polymers and Thickeners for Cosmetics, vol. 108, (May, 1993), pp. 95–114, 116–124, 127–130 & 132–135.
Finkel, Formulierung kosmetischer Sonnenschutzmittel, SÖFW–Journal, vol. 122, (1996), Month unknown, pp. 543–546 & 548.
"Kosmetische Färbemittel", Farbstoffkommission der Deutschen Forschungsgemeinschaft, Verlag Chemie, Weinheim, (1991), Month unknown, pp. 81–106.

* cited by examiner

Primary Examiner—Daniel S. Metzmaier
(74) Attorney, Agent, or Firm—John E. Drach; Steven J. Trzaska

(57) ABSTRACT

The invention relates to emulsion bases containing
(a) polyol poly-12-polyhydroxystearates,
(b) polyol esters selected from the group consisting of sorbitan esters, oligoglycerol esters and partial glycerides,
(c) citric acid esters,
(d) waxes and
(e) metal soaps.

The emulsion bases are distinguished by the fact that they enable both stable creams and lotions to be produced, irrespective of the polarity of the oils combined therewith.

7 Claims, No Drawings

W/O EMULSION BASES

BACKGROUND OF THE INVENTION

This invention relates generally to cosmetic preparations and more particularly to universally usable w/o emulsion bases.

From the physicochemical perspective, cosmetic preparations, such as creams and lotions for example, are emulsions of which there are two types, namely: water-in-oil (w/o) and oil-in-water (o/w) emulsions. Commercially, there is a particular interest in w/o emulsions which can differ greatly in their viscosity from solid creams through soft creams to thinly liquid lotions. An enormous number of suitable oil components, emulsifiers and auxiliaries and additives is available to the cosmetic chemist for the production of such preparations, his task being to combine them in such a way that a product with the requisite range of applications is obtained. This is sometimes a very laborious task, particularly when the goal is to produce products with a specific viscosity which they are able to retain for long periods, even when stored at elevated temperature, without becoming thinly liquid, gelling or separating. Another important requirement in the formulation of w/o emulsions is to adjust the sensorial properties of the emulsions to suit the user. A particular requirement in this regard is to combine oil components differing in polarity and spreading with one another in such a way that a so-called "spreading cascade" is formed [cf. U. Zeidler in Fette, Seifen, Anstrichmitt. 87, 403 (1985) and S. Wallat et al. in Parf. Kosm. 75, 768 (1994)]. Unfortunately, the oils are often difficult to incorporate together in a stable form because of their different polarities.

International patent application WO 95/34528 discloses w/o emulsions containing polyolpolyhydroxystearates. Other auxiliaries and additives which may be added include inter alia co-emulsifiers, such as for example citric acid esters, sorbitan esters, etc., fats and waxes and stabilizers, such as metal salts of fatty acids.

Accordingly, the complex problem addressed by the invention was to provide mixtures which, on the principle of a simple building block, would allow the production of storage-stable w/o emulsions differing in their viscosities and, at the same time, would also enables oils of different polarity to be incorporated.

DESCRIPTION OF THE INVENTION

The present invention relates to w/o emulsion bases containing (a) polyol poly-12-polyhydroxystearates,
(b) polyol esters selected from the group consisting of sorbitan esters, oligoglycerol esters and partial glycerides,
(c) citric acid esters,
(d) waxes and
(e) metal soaps.

It has surprisingly been found that mixtures of components (a) to (e), irrespective of the polarity of the oil components combined therewith, lead to w/o emulsions which are stable in their viscosity and stable in storage. If components (a) and (b+c+d+e) are mixed in the preferred ratio by weight of 10:90 to 30:70 or 40:60 to 60:40, both creams and lotions can be obtained in dependence upon the ratio by weight of aqueous to oil phase.

Polyol Poly-12-hydroxystearates

The polyol poly-12-hydroxystearates used as component (a) are known substances which are marketed, for example, under the name of Dehymuls® PGPH (cf. International patent application WO 95/34528 (Henkel)). The polyol component of the emulsifiers may be derived from substances which contain at least 2, preferably 3 to 12 and more preferably 3 to 8 hydroxyl groups and 2 to 12 carbon atoms. Typical examples are:

(a) glycerol and polyglycerol;
(b) alkylene glycols such as, for example, ethylene glycol, diethylene glycol, propylene glycol;
(c) methylol compounds such as, in particular, trimethylol ethane, trimethylol propane, trimethylol butane, pentaerythritol and dipentaerythritol;
(d) alkyl glucosides containing 1 to 22, preferably 1 to 8 carbon atoms and more preferably 1 to 4 carbon atoms in the alkyl group, for example methyl and butyl glucoside;
(e) sugar alcohols containing 5 to 12 carbon atoms, for example sorbitol or mannitol,
(f) sugars containing 5 to 12 carbon atoms, for example glucose or sucrose;
(g) aminosugars, for example glucamine.

Among the emulsifiers suitable for use in accordance with the invention, reaction products based on polyglycerol are particularly important by virtue of their excellent performance properties. It has proved to be of particular advantage to use selected polyglycerols which have the following homolog distribution (the preferred ranges are shown in brackets):

| | |
|---|---|
| glycerol | 5 to 35 (15 to 30) % by weight |
| diglycerols | 15 to 40 (20 to 32) % by weight |
| triglycerols | 10 to 35 (15 to 25) % by weight |
| tetraglycerols | 5 to 20 (8 to 15) % by weight |
| pentaglycerols | 2 to 10 (3 to 8) % by weight |
| oligoglycerols | to 100% by weight |

Sorbitan Esters

A group of suitable polyol esters which form component (b) are sorbitan esters which are reaction products of sorbitan with fatty acids and which correspond to general formula (I):

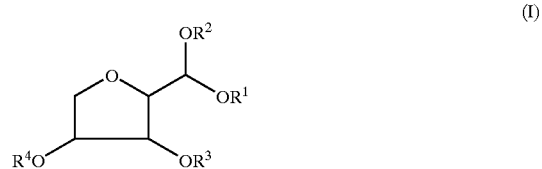

in which $R^1$, $R^2$, $R^3$ and $R^4$ independently of one another represent hydrogen or saturated and/or unsaturated, linear or branched acyl groups containing 6 to 22 carbon atoms, with the proviso that at least one of the substituents $R^1$ to $R^4$ is an acyl group. Typical examples are sorbitan esters derived from the following fatty acids: caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or as monomer fraction in the dimerization of unsaturated fatty acids. Sorbitan esters based on fatty acids containing 12 to 18 carbon atoms, such as for example lauric acid, cocofatty acid, palmitic acid, stearic acid, isostearic acid and oleic acid. Since the sorbitan has four primary hydroxyl groups which, basically, are all accessible to esterification, the sorbitan esters are generally mixtures of mono-, di- and triesters; full esters by contrast are only present in small quantities. So-called sesquiesters, i.e. sorbitan esters containing on average 1.5 ester groups are preferred.

Oligoglycerol Esters

Another group of suitable polyol esters are oligoglycerol esters which may be obtained by condensation of technical oligoglycerols with fatty acids containing 6 to 22 and preferably 12 to 18 carbon atoms. The oligoglycerol component may have a degree of self-condensation of 2 to 10 and preferably 2 to 5. Of particular advantage are esters which are derived from technical diglycerols or triglycerols and which are condensed with 1 to 6 and preferably 2 to 5 moles, based on free hydroxyl groups, of linear or branched fatty acids containing 12 to 18 carbon atoms. Typical examples are oligoglycerol esters based on technical di-/triglycerol mixtures with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or as monomer fraction in the dimerization of unsaturated fatty acids. Oligoglycerol esters based on palmitic acid, stearic acid, isostearic acid and mixtures thereof are particularly preferred.

Partial Glycerides

Partial glycerides, i.e. monoglycerides, diglycerides and technical mixtures thereof, which may also be used as polyol esters, may still contain small quantities of triglycerides from their production. The partial glycerides preferably correspond to formula (II):

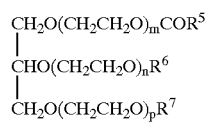

(II)

in which $R^5CO$ is a linear or branched, saturated and/or unsaturated acyl group containing 6 to 22 and preferably 12 to 18 carbon atoms, $R^6$ and $R^7$ independently of one another have the same meaning as $R^5CO$ or represent OH and the sum (m+n+p) is 0 or a number of 1 to 100 and preferably 5 to 25, with the proviso that at least one of the two substituents $R^6$ and $R^7$ represents OH. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Technical lauric acid glycerides, palmitic acid glycerides, stearic acid glycerides, isostearic acid glycerides, oleic acid glycerides, behenic acid glycerides and/or erucic acid glycerides which have a monoglyceride content of 50 to 95% by weight and preferably 60 to 90% by weight are preferably used.

Citric Acid Esters

Citric acid esters suitable for use as component (c) in accordance with the invention correspond to formula (III):

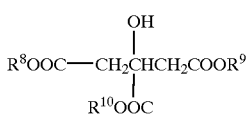

(III)

in which $R^8$, $R^9$ and $R^{10}$ represent hydrogen or a linear or branched alkyl and/or alkenyl group and/or the residue of a polyol containing 2 to 12 carbon atoms and 2 to 12, preferably 3 to 8 hydroxyl groups, with the proviso that at least one of the substituents $R^8$ to $R^{10}$ is not hydrogen. Typical examples are citric acid esters which may be derived from the following primary alcohols: caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of methyl esters based on fats and oils or aldehydes from Roelen's oxosynthesis or as monomer fraction in the dimerization of unsaturated fatty alcohols. Technical fatty alcohols containing 12 to 18 carbon atoms such as, for example, coconut, stearyl, cetearyl or tallow alcohol are preferred. Other suitable alcohol components are polyols, such as:

glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol;

sugars containing 5 to 12 carbon atoms, for example glucose or sucrose;

aminosugars, for example glucamine.

Since citric acid has three carboxyl groups which are all accessible to esterification, the citric acid esters can be mono-, di- or tricitrates and mixtures thereof. If polyols, for example trimethylol propane or pentaerythritol, are used as the alcohols, bridged complex esters can also be formed. A preferred embodiment of the invention is characterized by the use of citric acid esters obtained by co-condensation of citric acid with alcohols (for example coconut oil alcohol and stearyl alcohol) and polyols (for example TMP or pentaerythritol) [cf. DE-PS 1165574 (Dehydag)].

Waxes

Waxes in the context of the invention are preferably substances which are kneadable, firm to brittle and hard, coarsely to finely crystalline, translucent or opaque but not glass-like at 20° C., melt without decomposing above 40° C. and are of relatively low viscosity and non-stringing just above their melting point.

Typical examples of suitable waxes are natural vegetable or animal waxes, such as candelilla wax, carnauba wax, Japan wax, esparto grass wax, cork wax, guaruma wax, rice oil wax, sugar cane wax, ouricury wax, montan wax, bees wax, shellac wax, spermaceti, lanolin, uropygial fat, mineral waxes, such as ceresine or ozocerite, petrochemical waxes, such as petrolatum, paraffin waxes and microwaxes. Other suitable waxes are synthetic hard waxes, such as montan ester waxes, sassol waxes, hydrogenated jojoba waxes, polyalkylene waxes and polyethylene glycol waxes. Bees wax, lanolin and/or montan wax is preferably used.

Metal Soaps

Metal soaps which are present as stabilizing component (e) preferably correspond to formula (IV):

$$(R^{11}COO)_n\text{-}X \qquad (IV)$$

in which $R^8CO$ is a linear or branched, saturated or unsaturated acyl group containing 6 to 22 and preferably 12 to 18 carbon atoms, X is magnesium, aluminium or zinc and n is a number corresponding to the valency of X. Typical examples are the corresponding magnesium, aluminium and/or zinc salts of the following carboxylic acids: caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, ricinoleic acid, 12-hydroxystearic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or as monomer fraction in the dimerization of unsaturated fatty acids. Magnesium stearate, aluminium stearate or zinc stearate is preferably used.

W/O Emulsion Bases

A preferred embodiment of the invention is characterized by the use of emulsion bases which contain components (a) to (e) in the following quantities:

(a) 5 to 95, preferably 25 to 70 and more preferably 35 to 50% by weight of polyol poly-12-polyhydroxystearates, (b) 2 to 35, preferably 10 to 30 and more preferably 15 to 25% by weight of sorbitan esters, oligoglycerol esters and partial glycerides, (c) 1 to 40, preferably 5 to 30 and more preferably 10 to 20% by weight of citric acid esters, (d) 1 to 25, preferably 5 to 20 and more preferably 10 to 15% by weight of waxes and (e) 0.5 to 25, preferably 5 to 15% by weight of metal soaps, with the proviso that the quantities shown add up to 100% by weight, optionally with water and other auxiliaries and additives.

Commercial Applications

The emulsion bases according to the invention may be used for the production of a range of cosmetic preparations, including for example creams, lotions, emollients and the like, and may be used in quantities of normally 2 to 25% by weight and preferably 4 to 15% by weight, based on the particular preparation. The emulsion bases, but preferably the final formulations, may contain mild surfactants, oil components, co-emulsifiers, superfatting agents, pearlizing waxes, consistency factors, thickeners, polymers, silicone compounds, biogenic agents, antidandruff agents, film formers, preservatives, hydrotropes, solubilizers, UV protection factors, antioxidants, insect repellents, self-tanning agents, perfume oils, dyes and the like.

Typical examples of suitable mild surfactants, i.e. surfactants with particular dermatological compatibility, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, alkyl oligoglucosides, fatty acid glucamides, alkylamidobetaines and/or protein fatty acid condensates, preferably based on wheat proteins.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons.

Suitable co-emulsifiers are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) alkyl mono- and oligoglycosides containing 8 to 22 carbon atoms in the alkyl group and ethoxylated analogs thereof;

(3) products of the addition of 15 to 60 moles of ethylene oxide onto castor oil and/or hydrogenated castor oil;

(4) polyglycerol polyricinoleate, polyglycerol dimerate or mixtures thereof;

(5) products of the addition of 2 to 15 moles of ethylene oxide onto castor oil and/or hydrogenated castor oil;

(6) partial esters based on linear, branched, unsaturated or saturated $C_{6/22}$ fatty acids, ricinoleic acid, pentaerythritol, dipentaerythritol, sugar alcohols (for example sorbitol), alkyl glucosides (for example methyl glucoside, butyl glucoside, lauryl glucoside) and polyglucosides (for example cellulose);

(7) mono-, di- and trialkyl phosphates and mono-, di- and/or tri-PEG-phosphates and salts thereof;

(8) wool wax alcohols;

(9) polysiloxane/polyalkyl polyether copolymers and corresponding derivatives;

(10) mixed esters of pentaerythritol, fatty acids and fatty alcohol according to DE-PS 11 65 574 and/or mixed esters of fatty acids containing 6 to 22 carbon atoms and methyl glucose and

(11) polyalkylene glycols.

The addition products of ethylene oxide and/or propylene oxide with fatty alcohols, fatty acids, alkylphenols or with castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

$C_{8/18}$ alkyl mono- and oligoglycosides, their production and their use as surfactants are known from the prior art. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known by the CTFA name of Cocamidopropyl Betaine is particularly preferred. Other suitable emulsifiers are ampholytic surfactants. Ampholytic surfactants are surface-active compounds which, in addition to a $C_{8/18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{2,18}$ acyl sarcosine. Other suitable emulsifiers besides the ampholytic emulsifiers are quaternary emulsifiers, those of the esterquat type, more particularly those of the methyl-quaternized fatty acid triethanolamine ester salt type, being particularly preferred.

Superfatting agents may be selected from such substances as, for example, lecithin and also polyethoxylated or acylated lecithin derivatives and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylamino-hydroxypropyl diethylenetriamine (Cartaretine®, Sandoz A G), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes. Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Sun (UV) protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP-B1 0693471;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP-A1 0818450;

propane-1,3-diones such as, for example, 1-(4-tert.butylphenyl)-3-(4'-methoxyphenyl)-propane-1,3-dione;

ketotricyclo(5.2.1.0)decane derivatives as described in EP-B1 0694521.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble light-blocking pigments, i.e. finely dispersed metal oxides or salts, for example titanium dioxide, zinc oxide, iron oxide, aluminium oxide, cerium oxide, zirconium oxide, silicates (talcum), barium sulfate and zinc stearate, may also be used for this purpose. The particles should have a mean diameter of less than 100 nm, preferably between 5 and 50 nm and more preferably between 15 and 30 nm. They may be spherical in shape although ellipsoidal particles or other non-spherical particles may also be used. Other suitable UV filters can be found in P. Finkel's review in SOFW-Journal 122, 543 (1996).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to µmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehydes, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Fäbemittel" of the Farbstoffkommission der Deutschen Forschungs-gemeinschaft, Verlag Chemie, Weinheim, 1991, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be prepared by standard cold or hot processes and are preferably produced by the phase inversion temperature method.

Examples

The following 7 preparations were produced on the basis of the w/o emulsion bases according to the invention: (1,6,7) sun protection lotions, (2) moisturizing cream, (3) skin care lotion, (4) skin care cream, (5) soft cream. The viscosity of the preparations was determined by the Brookfield method in an RVF viscosimeter [23° C., spindle 5, 10 r.p.m. (Examples 1,3,6 and 7) or spindle TE with Heliopath (Examples 2,4,5)] both immediately and after storage for 1 to 2 weeks. The results are set out in Table 1.

TABLE 1

| Viscosity of w/o emulsions | | | | | | | |
|---|---|---|---|---|---|---|---|
| Composition/viscosity | 1 | 2 | 3 | 4 | 5 | 6 | 7 |
| Polyglyceryl-2 Polyhydroxystearate | 3.0 | 3.0 | 3.0 | 1.0 | 2.0 | 3.0 | 3.0 |
| Sorbitan Sesquioleate | 0.7 | 0.7 | 0.7 | 2.8 | 2.8 | — | — |
| Polyglyceryl-3 Diisostearate | — | — | — | — | — | 0.7 | — |
| Glyceryl Oleate | — | — | — | — | — | — | 0.5 |
| Dicocoyl Pentaerythrityl Distearyl Citrate | 0.3 | 0.3 | 0.3 | 1.2 | 1.2 | 0.3 | 0.3 |
| Beeswax | 0.5 | 0.5 | 0.5 | 2.0 | 2.0 | — | — |

TABLE 1-continued

Viscosity of w/o emulsions

| Composition/viscosity | 1 | 2 | 3 | 4 | 5 | 6 | 7 |
|---|---|---|---|---|---|---|---|
| Hydrogenated Castor Oil | — | — | — | — | — | 0.5 | 0.5 |
| Aluminium Stearate | 0.5 | 0.5 | 0.5 | 2.0 | 2.0 | 0.5 | 0.5 |
| Capric Caprylic Glycerides | 6.0 | — | — | — | — | 6.0 | 6.0 |
| Cocoglycerides | — | 3.0 | 4.0 | 3.0 | 3.0 | — | — |
| Almond Oil | — | 2.0 | 2.0 | 2.0 | 2.0 | — | — |
| Petrolatum | — | — | — | — | — | 10.0 | 10.0 |
| Octyldodecanol | 6.0 | — | 5.0 | — | — | — | — |
| Dicaprylyl Ether | — | 2.0 | — | 3.0 | 2.0 | — | — |
| Cyclomethicone | — | — | — | — | — | 5.0 | 5.0 |
| Octyl Stearate | — | 9.0 | 8.0 | 10.0 | 9.0 | — | — |
| Cetearyl Isononanoate | 5.1 | — | — | — | — | 5.1 | 5.1 |
| Tocopheryl Acetate | 1.0 | — | — | 1.0 | — | 1.0 | 1.0 |
| Isoamyl p-Methoxycinnamate | 7.0 | — | — | — | — | 7.0 | 7.0 |
| Zinc Oxide | 6.0 | — | — | — | — | 6.0 | 6.0 |
| Chitosan (1% by weight) | — | — | — | 5.0 | — | — | — |
| Magnesium Sulfate-7 Hydrate | — | 1.0 | 1.0 | 1.0 | — | — | — |
| Sorbitol (70% by weight) | — | 3.0 | — | — | — | — | — |
| Glycerin (86% by weight) | — | 3.0 | 5.0 | 3.0 | 5.0 | — | — |
| Water, preservative | | | | to 100 | | | |
| Viscosity [Pas] | | | | | | | |
| - after 1 d | 10.0 | 62.5 | 11.2 | 137.5 | 62.5 | 10.0 | 10.1 |
| - after 1 w | 11.2 | 62.5 | 11.2 | 150.0 | 63.5 | 11.2 | 11.3 |
| - after 2 w | 11.5 | 62.5 | 12.0 | 150.0 | 64.0 | 11.5 | 11.5 |

What is claimed is:

1. A composition comprising: (a) from about 5 to about 95% by weight of a polyol poly-12-polyhydroxystearate; (b) from about 2 to about 35% by weight of a polyol ester selected from the group consisting of a sorbitan ester, an oligoglycerol ester, a partial glyceride, and mixtures thereof; (c) from about 1 to about 40% by weight of a citric acid ester; (d) from about 1 to about 25% by weight of a wax; and (e) from about 0.5 to about 25% by weight of a metal soap, all weights being based on the total weight of the composition.

2. The composition of claim 1 wherein component (a) is a polyglycerol poly-12-hydroxystearate.

3. The composition of claim 1 wherein the sorbitan ester is a compound of the formula (I):

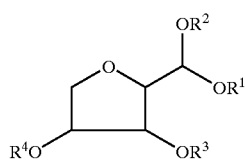
(I)

wherein each of $R^1$, $R^2$, $R^3$ and $R^4$ is independently hydrogen or a saturated and/or unsaturated, linear or branched acyl group having from 6 to 22 carbon atoms, with the proviso that at least one of $R^1$ to $R^4$ is an acyl group.

4. The composition of claim 1 wherein component (b) is an oligoglycerol ester of a $C_{6-22}$ fatty acid.

5. The composition of claim 1 wherein the partial glyceride is a compound of the formula (II):

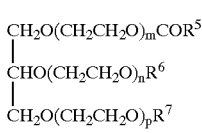
(II)

wherein $R^5CO$ is a linear or branched, saturated and/or unsaturated acyl group having from 6 to 22 carbon atoms; each of $R^6$ and $R^7$ is independently OH or $R^5CO$ as defined above; with the proviso that the sum of m+n+p is 0 or a number from 1 to 100 and that at least one of $R^6$ and $R^7$ is OH.

6. The composition of claim 1 wherein the citric acid ester is a compound of the formula (III):

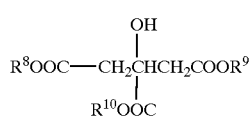
(III)

wherein each of $R^8$, $R^9$ and $R^{10}$ is independently hydrogen, a linear or branched alkyl and/or alkenyl group and/or the residue of a polyol having 2 to 12 carbon atoms and 2 to 12 hydroxyl groups, with the proviso that at least one of $R^8$, $R^9$ and $R^{10}$ is not hydrogen.

7. The composition of claim 1 wherein the wax is selected from the group consisting of beeswax lanolin, monton wax, and mixtures thereof.

* * * * *